(12) United States Patent
Nelson

(10) Patent No.: US 8,034,833 B2
(45) Date of Patent: Oct. 11, 2011

(54) PHOSPHORUS BINDER FOR TREATMENT OF RENAL DISEASE

(75) Inventor: Deanna Jean Nelson, Raleigh, NC (US)

(73) Assignee: Biolink Life Sciences, Inc., Cary, NC (US)

( * ) Notice: Subject to any disclaimer, the term of this patent is extended or adjusted under 35 U.S.C. 154(b) by 691 days.

(21) Appl. No.: 12/077,777

(22) Filed: Mar. 20, 2008

(65) Prior Publication Data

US 2009/0239914 A1  Sep. 24, 2009

(51) Int. Cl.
*A61K 31/42* (2006.01)
(52) U.S. Cl. ........................................ 514/375
(58) Field of Classification Search ............ 514/375
See application file for complete search history.

(56) References Cited

U.S. PATENT DOCUMENTS 5,496,545 A * 3/1996 Holmes-Farley et al. . 424/78.11
2006/0276538 A1* 12/2006 Ashmead et al. ............. 514/492

* cited by examiner

*Primary Examiner* — Taofiq A Solola
(74) *Attorney, Agent, or Firm* — Casimir Jones SC

(57) ABSTRACT

The present invention relates to oral compositions which are useful for binding phosphorus in ingesta, and inhibiting absorption of phosphorus from the gastrointestinal tract of subjects. A method for binding phosphorus in ingesta and inhibiting its absorption from the gastrointestinal tract is also provided. The dietary supplements and pharmaceutical products and methods of the present invention are particularly useful in the treatment of hyperphosphatemia of chronic uremia and reducing serum phosphorus levels in patients requiring such therapy.

4 Claims, No Drawings

PHOSPHORUS BINDER FOR TREATMENT OF RENAL DISEASE

CROSS-REFERENCE TO RELATED APPLICATION

This application claims priority of filing by Provisional Application Ser. No. 60/91973 of the same title, filed Mar. 22, 2007.

FIELD OF THE INVENTION

The present invention relates to oral compositions which are useful for binding phosphorus in ingesta, and inhibiting absorption of phosphorus from the gastrointestinal tract. A method for binding phosphorus in ingesta and inhibiting its absorption from the gastrointestinal tract is also provided. The dietary supplements and pharmaceutical products and methods of the present invention are particularly useful in the treatment of hyperphosphatemia of chronic uremia and reducing serum phosphorus levels in subjects requiring such therapy.

BACKGROUND OF THE INVENTION

Phosphorus, the sixth most abundant element in the human body, is critical for bone mineralization, cellular structure, genetic coding, and energy metabolism. Approximately 1,000 g of phosphorus, constituent in a variety of organic and inorganic forms, is present in an adult human. About 80-90% of the phosphorus is in bone, 10-14% is intracellular, and the remaining 1% is extracellular.

Phosphorus is present in nearly all foods, and absorption of dietary phosphorus from ingesta in the gastrointestinal (GI) tract is very efficient. Normal daily dietary intake varies from 800-1,500 mg of phosphorus. Typically, 70-90% of dietary phosphorus is absorbed, primarily from the jejunum, duodenum, and proximal ileum of the GI tract, although some absorption continues throughout the remainder of the intestinal tract. A small amount of GI excretion occurs.

In the normal adult human, serum phosphorus levels range from 2.5 to 4.5 mg/dL (0.81 to 1.45 mmol phosphorus/L). (Normal serum levels are typically 50% higher in infants and 30% higher in children due to growth hormone effects.) A condition of phosphorus homeostasis is normally maintained in the body of a subject, wherein the amount of phosphorus absorbed from the gastrointestinal tract approximately equals the amount excreted via the kidney. In addition, cellular release of phosphorus is balanced by uptake in other tissues. Hormonal control is provided by parathyroid hormone.

Since the kidney plays a central role in maintaining phosphorus homeostasis, kidney dysfunction is often accompanied by increased phosphorus retention by the body. In early kidney dysfunction, compensatory physiological responses allow for a continued match between urinary phosphorus excretion and phosphorus absorption from the gastrointestinal (GI) tract. With more advanced renal failure, however, elevated serum phosphorus is a predictable co-morbidity.

Hyperphosphatemia is a disease state in which there is an abnormally elevated serum phosphorus (Pi) level in the body. Hyperphosphatemia is a particular problem of chronic kidney disease (CKD) patients who are treated using dialysis. Conventional dialysis fails to reduce levels of phosphorus in the blood, and serum phosphorus levels increase with time. Significant hyperphosphatemia is considered present when serum phosphorus levels are greater than about 5 mg/dL in adults or 7 mg/dL in children or adolescents. [National Kidney Foundation. Am J Kidney Dis 2003; 42 (Suppl 3):S1-S201.]

In patients with CKD, phosphorus retention (as evidenced by abnormally elevated serum phosphorus levels) may contribute to progression of renal failure and is a major factor in the development of secondary hyperparathyroidism, renal osteodystrophy, and soft tissue calcification. [Block G A, Klassen P S, Lazarus J M, Ofsthun N, Lowrie E G, Chertow G. J Am Soc Nephrol 2004 August; 15(8): 2208-2218.] Prevention of phosphorus retention with dietary and pharmacological means is frequently required to prevent or reverse secondary hyperparathyroidism and the morbidities and mortality risks associated with it. [Qunibi W Y. Kidney Int 66 (Suppl 90): S8-S12. Alfrey A C. Kidney Int 66 (Suppl 90): S13-S17.] Phosphorus (Pi) binders which bind dietary phosphorus in the gastrointestinal tract are, therefore, clinical mainstays in restoring phosphorus balance and preventing hyperphosphatemia in the roughly 450,000 end-stage renal disease (ESRD) patients in the United States.

Phosphorus Binders. Phosphorus binders are ingested orally by a subject to bind dietary phosphate and convert it to insoluble phosphate salts, thus preventing its absorption from the GI tract. Phosphorus binding is a chemical reaction between dietary phosphorus and a cation of the binder compound, resulting in the formation of insoluble and hence unabsorbable phosphate compounds; adsorption of phosphorus-containing anions on the surface of binder particles; or a combination of both processes. Two classes of phosphorus binders are known: metal salts and cationic polymers. Known metal salts with phosphate-binding properties are calcium salts, including calcium acetate, calcium carbonate, calcium citrate, calcium alginate, calcium gluconate, calcium lactate, and calcium sulfate; magnesium salts, including magnesium carbonate, and magnesium hydroxide; aluminum salts, including aluminum hydroxide and aluminum carbonate; ferric citrate and ferric acetate; lanthanum salts, including lanthanum carbonate; and zirconium salts. Cationic polymers that exhibit phosphorus binding include high molecular weight polymers having multiple amine substituents, such as, by way of example, a polymer known as sevelamer hydrochloride (marketed as "RenaGel®" by Genzyme, Inc.).

In U.S. Pat. No. 4,889,725 Veltman discloses a means for promoting the neutralization reaction between particulate calcium carbonate and ionized phosphate by adding a material formed by the reaction of particulate calcium carbonate and dilute hydrofluoric acid. The products of this invention are useful in lowering serum phosphorus levels in patients undergoing renal dialysis, and are also useful as antacids.

A common treatment for controlling Pi levels is disclosed in U.S. Pat. No. 4,870,105 to Fordtran, which discloses a calcium acetate phosphorus binder for oral administration to an individual for the purpose of inhibiting gastrointestinal absorption of phosphorus. It further discloses a method of inhibiting gastrointestinal absorption of phosphorus, comprising administering orally the calcium acetate phosphorus binder, preferably close in time to food and beverage consumption. Likewise, U.S. Pat. No. 6,576,665 to Dennett, Jr. et al. discloses a composition for inhibiting gastrointestinal absorption of phosphorus in an individual. The composition includes a quantity of calcium acetate sufficient to bind the phosphorus and having a bulk density of between 0.50 kg/L and 0.80 kg/L and is dimensioned to form a caplet for fitting within a capsule. Further provided is a method for administering the calcium acetate composition. Likewise, U.S. Pat. No. 6,875,445 to Dennett, Jr., et al. discloses a composition for binding phosphorus within the gastrointestinal tract of an individual. The composition includes a quantity of calcium acetate having a specific bulk density sufficient to bind the phosphorus in the gastrointestinal tract of an individual. Further provided is a method for administering the calcium acetate composition.

U.S. Pat. No. 6,160,016 to DeLuca discloses a calcium formate composition for oral administration to an individual for the purpose of inhibiting gastrointestinal absorption of phosphorus. It further discloses a method of inhibiting gastrointestinal absorption of phosphorus, comprising administering orally the composition, preferably close in time to food and beverage consumption. Likewise, U.S. Pat. No. 6,489,361, to DeLuca discloses a calcium formate composition for oral administration to an individual for the purpose of inhibiting gastrointestinal absorption of phosphorus. Further, DeLuca discloses a method of inhibiting gastrointestinal absorption of phosphorus, comprising administering orally the calcium formate composition of his invention, preferably close in time to food and beverage consumption.

U.S. Pat. No. 4,689,322, to Kulbe et al. provides calcium salts or calcium mixed salts of polymeric, anionic carboxylic acids and/or an ester of sulfuric acid, and methods for their preparation and use, discloses a pharmaceutical product which contains at least a calcium salt or a calcium mixed salt of a natural or chemically modified polymeric, anionic carboxylic acid and/or an ester of sulfuric acid, and additive materials and/or carrier materials. There are further disclosed calcium salts, and methods of preparation thereof, comprised of polymannuronic acid, polygalacturonic acid, polyglucuronic acid, polyguluronic acid, the oxidation products of homoglycans, the oxidation products of heteroglycans, or their mixtures, for controlling the levels of phosphorus, calcium and iron in patients with chronic uremia and/or the control of the oxalate and/or phosphate of the blood in kidney stone prophylaxis.

U.S. Pat. No. 6,887,897 to Walsdorf and Alexandrides discloses a calcium glutarate supplement and its use for controlling phosphate retention in patients on dialysis and suffering from renal failure and associated hyperphosphatemia. Therapeutic benefit can be realized by administering a calcium glutarate compound orally to a patient to increase available calcium and contact and bind with ingested phosphorus in the patient's digestive tract, and thereby prevent its intestinal absorption.

The Pi binding properties of magnesium salts have been studied by Fine et al. in acute studies involving normal subjects. [Fine K D, Santa Ana C A, Porter J L, Fordtran J S. Intestinal absorption of magnesium from food and supplements. J Clin Invest 1991; 88: 396-402.] They found a dose-dependent decrease in Pi absorption from ingesta that ranged from 75% Pi absorption with placebo to 28% Pi absorption with 77 mEq magnesium acetate (MgAc) per os. Fine stated that Pi absorption by magnesium acetate was comparable to that of calcium acetate, a current standard of care. However, Fine rejected use of magnesium acetate, because "the risk of hypermagnesemia and diarrhea from MgAc ingestion would likely limit the clinical usefulness of MgAc as a P binder." [ibid, page 401, column 1, paragraph 4]

Several investigators have evaluated the use of orally administered magnesium (Mg) hydroxide- or carbonate-containing Pi binders in the treatment of ESRD patients undergoing dialysis. Guillot et al., treated nine patients undergoing conventional hemodialysis with oral magnesium hydroxide for three to five weeks. [Guillot A P, Hood V L, Runge C F, Gennari F J. The use of magnesium-containing phosphate binders in patients with end-stage renal disease on maintenance hemodialysis. Nephron 1982; 30:114-117.] Using doses averaging 734 mg of elemental Mg/day and concurrent dialysis with dialysate having Mg concentrations of 1.2 to 1.8 mg/dl, the serum Pi levels fell from a control (no binders) value of 9.0 mg/dL to 8.1 mg/dL as a result of treatment. The mean serum Mg levels were 4.32 mg/dL. Four of nine patients developed diarrhea. In contrast to the Guillot study, Mactier et al. observed no effect of oral choline magnesium trisalicylate (trilisate) on serum Pi levels in either hemodialysis or peritoneal dialysis patients. [Mactier R A, Leung A C T, Henderson I S, and Dobbie J W. Control of hyperphosphatemia in dialysis patients: Comparison of aluminum hydroxide, calcium carbonate, and magnesium trilisate. Dial Transplant 1987; 16: 599-601.] Adverse findings were reported by Oe et al., who studied eighteen patients undergoing conventional hemodialysis who were switched from oral $Al((OH)_3$ to $Mg(OH)_2$. [Oe P L, Lips P, van der Meulen J, de Vries P M J M, van Bronswuk H. Long-term use of magnesium hydroxide as a phosphate binder in patients on hemodialysis. Clin Nephrol 1987; 28: 180-185.] Serum Pi levels rose from 4.3 to 6.1 mg/dL despite an average daily intake of 991 mg of elemental Mg and use of a dialysate lacking Mg. The serum Mg level averaged 4.3 mg/dL during $Mg(OH)_2$ treatment. The potassium levels were significantly higher when patients received $Mg(OH)_2$ compared to the control phase (5.7±0.3 vs. 5.1±0.4 mEq/L). O'Donovan et al. switched 28 patients undergoing conventional hemodialysis from oral $Al(OH)_3$ to oral $MgCO_3$ in combination with a Mg-free dialysate. [O'Donovan R, Baldwin D, Hammer M, Moniz C, Parsons V. Substitution of aluminium salts by magnesium salts in control of dialysis hyperphosphataemia. Lancet 1986; 1: 880-882.] Over the two-year study period, Ca, P, and Mg levels were well controlled and not different from those in the control phase. The amount of elemental Mg used varied between 155 to 465 mg/day. Diarrhea was mild and transient. Similar data were reported by Moriniere et al. [Moriniere P, Vinatier I, Westeel P F. Magnesium hydroxide as a complementary aluminum-free phosphate binder to moderate doses of oral calcium in uraemic patients on chronic haemodialysis. Nephrol Dial Transplant 1988; 3: 651-656.] They also reported severe hyperkalemia as high as 8 mEq/L in many patients, the etiology of which was unclear. More recently, this same group performed a controlled study in which patients were either treated with $CaCO_3$ plus $Mg(OH)_2$ as needed or $Mg(OH)_2$ alone and 1-alpha-hydroxyvitamin $D_3$. [Morniere P, Maurouard C, Boudailliez B, Westeel P, Achard J, Boitte F, El Esper N, Compagnon M, Maurel G, Bouillon R, Pamphile R, Fournier A. Prevention of hyperparathyroidism in patients on maintenance dialysis by intravenous 1-alpha-hydroxyvitamin $D_3$ in association with $Mg(OH)_2$ as sole phosphate binder. Nephron 1992; 60: 154-163.] Neither the combination of oral calcium carbonate/magnesium hydroxide nor magnesium hydroxide alone was effective in suppressing parathyroid hormone (PTH) secretion, and uncontrolled hyperphosphatemia forced a reduction in the dose of 1-alpha-hydroxyvitamin $D_3$. Delmez et al. showed that magnesium carbonate was well-tolerated and controlled Pi and Mg levels when given in conjunction with a dialysate having a Mg concentration of 0.6 mg/dL. [Delmez J A, Kelber J, Norword K Y, Giles K S, Slatopolsky E. Magnesium carbonate as a phosphorus binder: A prospective, controlled, crossover study. Kidney Int 1996; 49: 163-167.] In addition, Delmez showed that oral magnesium carbonate (dose, 465±52 mg/day elemental Mg) allowed a decrease in the amount of elemental calcium ingested from 2.9±0.4 to 1.2±0.2 g/day (P<0.0001). Moreover, the combined treatment allowed an increase in the maximum dose of intravenous calcitriol without causing hypercalcemia.

Recently, Fresenius Medical Care A G & Co. KGaA (Bad Homburg Germany) received regulatory approval from Germany's Federal Institute for Drugs and Medical Devices (Bundesinstitut für Arzneimittel und Medizinprodukte) for a new phosphate binding agent. The Fresenius drug, called "OsvaRen," is a phosphate binding agent that is made from a combination of calcium acetate and magnesium carbonate.

U.S. Pat. No. 6,926,912 to Roberts et al. discloses a non-aluminum containing mixed metal compound for pharmaceutical use, which may be a mixed metal hydroxy carbonate containing magnesium and iron, and may have a hydrotalcite structure, preferably a non-aged hydrotalcite structure. Other metals, including calcium, lanthanum and cerium, may also be used. U.S. Pat. No. 4,988,569 to Okazaki et al. discloses a phosphate adsorbent comprising a magnesium oxide-titanium dioxide complex as an active ingredient and a phosphate adsorbent having said complex deposited on active carbon.

Phosphate-binding polymers include sevelamer, which is marketed under the brand name RenaGel® (Genzyme, Waltham Mass.), Oxasorb®, and polymers prepared using the methods disclosed in U.S. Pat. Nos. 5,496,545, 5,667,775, 6,083,495; 6,509,013, 6,726,905, 6,844,372, 6,858,203, and 7,087,223. U.S. Pat. No. 6,132,706 to Hider and Canas-Rodriguez discloses methods of medical treatment for excess phosphate using guanidine-containing polymers. U.S. Pat. Nos. 6,383,518 and 6,697,087, both to Matsuda and Kubota, disclose phosphate-binding polymer preparations. In U.S. Pat. No. 7,014,846 Holmes-Farley et al. disclose phosphate-binding polymers for oral administration.

L-Carnitine. L-(−)-Carnitine is a vitamin-like nutrient that is essential for energy production and fat metabolism in the physiological systems of birds, fish, and mammals and has the structure:

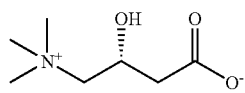

For humans, L-carnitine is supplied to the body through both endogenous synthesis (about 25% of adult daily requirement) and food intake (about 75% of adult daily requirement). Meats, in particular beef and lamb, are the major dietary sources of L-carnitine. (Fruits and vegetables are poor dietary sources of L-carnitine.)

Within the human body, the major sites of L-carnitine biosynthesis are the liver and kidney, and these organs synthesize sufficient L-carnitine for local use and for export to other tissues, including the muscles and heart. Biosynthesis also takes place in the brain and testes. Biosynthesis requires lysine, methionine, vitamin C, iron, vitamin $B_6$, and niacin. Dysfunction of the liver or kidney, such as cirrhosis of the liver or chronic kidney disease, may restrict the biosynthesis of L-carnitine and alter the diet, causing concomitant, deleterious L-carnitine deficiency.

Supplemental L-carnitine is available and has been used to mitigate L-carnitine deficiency. However, conventional L-carnitine compositions exhibit noxious odor and taste, as well as hygroscopicity. After ingestion, supplemental L-carnitine has a bioavailability that ranges between about 3% and about 20% of the administered dose.

L-Carnitine functions as a requisite mediator of acyl transport and accepts acyl groups from a variety of acylCoA derivatives in cells and tissues throughout the body. In humans, the transport activity of L-carnitine is particularly important in working muscle, for example, in the muscles throughout the body and the heart. Both types of tissues are dependent on fatty acid metabolism for energy supply, and L-carnitine mediates the translocation of fatty acyl groups across mitochondrial membranes to the sites of oxidation in the mitochondria. In addition, L-carnitine shuttles short chain fatty acids from inside the mitochondria to the cytosol.

A physiologically adequate concentration of L-carnitine is required to provide nutritional support for producing energy in muscles and heart, for mitochondrial long-chain fatty acid oxidation, buffering of the mitochondrial acyl CoA/CoA couple, scavenging acyl groups, peroxysomal fatty acid oxidation, branched-chain amino acid oxidation, and membrane stabilization.

The kidneys are sites of endogenous synthesis of L-carnitine as well of organs of excretory regulation. Under normal physiological conditions, 90% to 95% of the L-carnitine which undergoes glomerular filtration is subsequently reabsorbed by the renal tubules, with the balance excreted in the urine either as acetyl L-carnitine (the major form) or as L-carnitine. Individuals with chronic kidney disease (CKD) exhibit dysregulation of L-carnitine metabolism concomitant with reduction in glomerular filtration rate and other symptoms of renal failure. As a result, the concentration of free L-carnitine in the blood is lowered and the concentrations of L-carnitine esters in the blood are raised. In addition, progressive damage of the renal parenchyma leads to a loss of renal capacity to synthesize L-carnitine, reducing the intracellular L-carnitine concentration. Moreover, maldigestion, impaired absorption by the small intestine in uremia, and restrictions in dietary protein intake may contribute to an increasing L-carnitine deficiency in CKD patients. Finally, CKD patients who undergo hemodialysis lose L-carnitine during the dialysis procedure in excess of the endogenous synthesizing capacity. All of these factors render individuals with renal disease deficient in L-carnitine.

Because L-carnitine functions as a requisite mediator of acyl transport in the body, an L-carnitine deficiency is a serious physiological disorder. Individuals who suffer from L-carnitine deficiency are afflicted with muscle weakness (myasthenia), accompanied by an accumulation of lipids in specific types of muscle fibers. Severe L-carnitine deficiency may present as myasthenia gravis. Individuals who suffer from systemic L-carnitine deficiency and also secondary L-carnitine deficiency associated with organic acidemias may experience vomiting, stupor, confusion and in severe or prolonged occasions of systemic L-carnitine deficiency accompanied by stressful stimuli, coma in encephalopathic episodes.

It is known that increasing the serum L-carnitine concentration to more normal values provides significant benefit to individuals with renal disease. For example, intravenous administration of L-carnitine has been reported to decrease total cholesterol and LDL cholesterol while significantly increasing HDL cholesterol. [M. Bulla et al., "Dysregulation of carnitine metabolism in renal insufficiency," pages 177-194 in *Carnitine: Pathobiochemical Basics and Clinical Applications*, H. Seim and H. Loster, Eds. Ponte Press, Bochum, Germany, 1996] Likewise, Golper et al. have reported that intravenous administration of L-carnitine reduced the serum phosphate concentrations significantly. [T. A. Golper et al. "Multicenter trial of L-carnitine in maintenance hemodialysis patients. II. Clinical and biochemical effects." Kidney Intl 1990; 38: 912-918] Similarly encouraging observations have been reported with regard to cardiomyopathy, muscular myasthenia, hypotension and arrhythmia in CKD patients undergoing hemodialysis.

The ideal Pi binder should bind most dietary phosphorus in the gastrointestinal tract without producing significant adverse effects. It should also be relatively inexpensive, because most dialysis patients usually consume relatively large daily doses of the binder. Further, if components in the ideal Pi binder are absorbed from the gastrointestinal tract, these moieties should have beneficial physiological activities. Unfortunately, none of the currently used Pi binders fulfill all of these requirements. It would be very useful, therefore to have a Pi binder which binds dietary phosphorus more effectively, thus enabling use of lower doses, which does not have the risks associated with ingestion of conventional Pi binders, and which has pluripotent benefits to the subject. The present invention answers this unmet need.

SUMMARY OF THE INVENTION

In patients with impaired kidney function, the normal homeostasis of uptake and excretion of phosphates is typically impaired, leading to hyperphosphatemia and associated pathologies. It is an object of the present invention to control the uptake of dietary phosphates to abate, ameliorate, and prevent hyperphosphatemia. It is a further object to provide a phosphate binding composition that reduces the amount of dietary phosphate absorbed from the alimentary tract to achieve and sustain a balance of phosphate systemically in the body of a mammal. It is a still further object to provide phosphate binders that provide supplemental L-carnitine, a physiological substance that is often deficient in subjects having renal disease. It is an object of the present invention to provide phosphate binders that obviate side effects of conventional binders such as magnesium acetate and calcium acetate, which may cause diarrhea or constipation, respectively, or gastric irritation. A further object of the present invention is to provide phosphate binders that obviate side effects of conventional cationic polymers that are conventionally used as Pi binders, such as RenaGel and related resins, which may cause intestinal irritation and ulceration, sometimes resulting in death.

The present invention provides a composition for reducing the amount of dietary phosphorus absorbed from the alimentary tract comprising a combination of cationic phosphate binders and, optionally, a dithiolane carboxylate salt. In one embodiment, the combination of cationic phosphate binders comprises an L-carnitine alkaline earth metal salt of an organic acid and a second, conventional phosphate binder. In another embodiment, the combination of cationic phosphate binders comprises an L-carnitine calcium salt of an organic acid and an L-carnitine magnesium salt of an organic acid. In yet another embodiment, the combination of cationic phosphate binders comprises an L-carnitine calcium salt of an organic acid, and a magnesium dithiolane carboxylate. Of particular efficacy in scavenging dietary phosphate are combinations of L-carnitine calcium salts and L-carnitine magnesium salts or L-carnitine calcium salts and a magnesium dithiolane carboxylate, since these combinations provide exogenous, odorless and tasteless L-carnitine, calcium, and magnesium, each of which is active in phosphate binding, together with L-carnitine, which after absorption from the intestine provides beneficial correction of metabolic disorders, neurological dysfunction, and immune dysfunction. In a preferred embodiment, an odorless and tasteless L-carnitine calcium salt and a magnesium salt such as an L-carnitine magnesium salt or a magnesium dithiolane carboxylate are combined in a capsule, pill, or elixir, or as a direct additive to food. The dithiolane carboxylate salt in such embodiment will have an aliphatic content of a 4-8 carbon chain, and has the following structure:

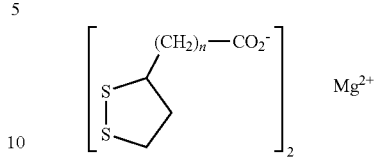

wherein n is an integer having a value of 1-8. In certain preferred embodiments of the present invention, the aliphatic content of the carbon chain of the dithiolane carboxylate molecule may vary from 4 carbon atoms to about 8 carbon atoms. A most preferred embodiment of the dithiolane carboxylate salt is magnesium alpha-lipoate (wherein n is 4), which in addition to its phosphorus binding has therapeutically beneficial antioxidant properties.

In certain embodiments, the combination of cationic phosphate binders comprises an L-carnitine alkaline earth metal salt of an organic acid and a second, conventional phosphate binder. In these embodiments, the alkaline earth metal of the L-carnitine alkaline earth metal salt of an organic acid is calcium or magnesium, and the salt of the organic acid is selected from the group consisting of acetate, propionate, butyrate, In certain embodiments, a phosphate binding composition of the present invention comprises an L-carnitine calcium salt of an organic acid and an L-carnitine magnesium salt of an organic acid. The salt component of the L-carnitine calcium salt may be identical to or different from the salt component of the L-carnitine magnesium salt. Preferably, in these embodiments the L-carnitine calcium salt and the L-carnitine magnesium salt are administered orally in a ratio of about 10:1 to 1:10 by molar weight.

In certain other embodiments, a phosphate binding composition of the present invention comprises an L-carnitine calcium salt of an organic acid and a dithiolane carboxylate salt wherein the dithiolane carboxylate salt is a magnesium dithiolane carboxylate salt. Preferably, in these embodiments the L-carnitine calcium salt and the magnesium dithiolane carboxylate salt are administered orally in a ratio of about 10:1 to 1:10 by molar weight.

In the method of the present invention, a composition as described hereinabove is administered to a subject by oral ingestion either concomitantly with food or close in time to the consumption of dietary phosphate-containing food or beverage. The composition, so administered, may be regarded either as a food additive, a substance that is generally regarded as safe (i.e., a GRAS substance), or a drug within the meaning of Title 21 of the Code of Federal Regulations (CFR).

DETAILED DESCRIPTION OF THE INVENTION

The present invention relates to a composition comprising a combination of cationic phosphate binders for oral administration to a subject. The composition is useful for reducing phosphorus absorption from the GI tract.

The present invention also relates to a method of inhibiting gastrointestinal phosphorus absorption. The method of the present invention is based on the demonstration that a composition comprising a first quantity of L-carnitine, a second quantity of a second cationic phosphate-binding agent, and a third quantity of a third cationic phosphate-binding agent is an effective binder of dietary phosphorus when the composition is administered orally to a subject. The method comprises orally administering a quantity of the composition sufficient to bind with phosphorus in the GI tract and prevent its absorption. Preferably, the dose of the composition is between about 0.1 and 15 g and is administered in a pharmaceutically acceptable oral dosage form (i.e., a tablet, gelatin capsule, elixir, and so forth). In a most preferable embodiment of the present invention, the oral dose is ingested close in time with food and/or beverage consumption.

In addition, the present invention relates to a method of reducing serum phosphorus levels in a warm-blooded animal comprising treating the animal with a therapeutically effective amount of a composition comprising a first quantity of an L-carnitine calcium salt and a second quantity of a dithiolane carboxylate salt.

The term "phosphorus," in defining use of the composition as a phosphorus binder, is intended to embrace both inorganic and organic anions of phosphorus in the various forms that are capable of electrostatic reaction with a phosphorus-binding agent including, by way of example, phosphate ($H_2PO_4^{1-}$, $HPO_4^{2-}$, and $PO_4^{3-}$), pyrophosphate ($P_2O_7^{4-}$), and the like.

The term "phosphate," in defining use of the composition as a phosphate binder, is intended to embrace both inorganic and organic anions of phosphorus in the various forms that are capable of electrostatic reaction with a phosphate-binding agent including, by way of example, phosphate ($H_2PO_4^{1-}$, $HPO_4^{2-}$, and $PO_4^{3-}$), pyrophosphate ($P_2O_7^{4-}$), and the like.

The term "phosphorus binding agent" or "phosphorus binder" or "phosphate binder," as it relates to the present invention, includes, by way of example, L-carnitine and L-carnitine alkaline earth metal salts such as L-carnitine calcium acetate, L-carnitine calcium salts of organic acids of the tricarboxylic acid cycle, L-carnitine calcium galactarate, L-carnitine magnesium citrate, and L-carnitine magnesium galactarate. The term also includes, by way of example, calcium salts such as calcium carbonate, calcium acetate, calcium citrate, calcium formate, calcium gluconate, calcium lactate, calcium glutarate, or calcium succinate. The term also includes, by way of example, magnesium salts such as magnesium carbonate, magnesium hydroxide, magnesium acetate, and magnesium succinate; as well as lanthanum salts, such as lanthanum carbonate. Also within the scope of this invention are hydrates, crystalline forms, and polymorphic forms of the aforementioned metal salts, metal salt-containing compositions having specific bulk densities or tap densities, and metal-salt containing compositions having specific particle sizes. Further included within the scope of this invention are metal salt-containing compositions coated with pharmaceutically acceptable materials intended to modify the release and/or bioavailability of the metal salt (e.g., Eudragit, microcrystalline cellulose, hydroxypropylmethylcellulose phthalate, and so forth).

The term "phosphorus binding agent" or "phosphorus binder" or "phosphate binder," as it relates to the present invention, also includes cationic polymers that bind phosphate, including by way of example, sevelamer, sevelamer hydrochloride, a polymer marketed as RenaGel®, a cationic polymer that is marketed under the brand name Oxasorb®, and polymers prepared using the methods disclosed in U.S. Pat. Nos. 5,496,545, 5,667,775, 6,083,495, 6,132,706, 6,383,518, 6,509,013, 6,697,087, 6,858,203 and 7,014,846.

By the term "dithiolane carboxylate salt" is meant a compound having the general formula:

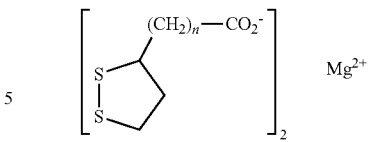

wherein n is an integer from 1 to 8. In general, dithiolane carboxylic acids may be purchased from chemical supply houses or may be prepared as described by Guillonneau et al. [Guillonneau, C, Charton, Y, Ginot, Y-M, Fouquier-d'Herouel, M-V, Bertrand, M, Lockhart, B, Lestage, P, and Goldstein, S. 2003. Synthesis and pharmacological evaluation of new 1,2-dithiolane based antioxidants. Eur J Med Chem 38: 1-11.] A dithiolane carboxylic acid is converted to a metal dithiolane carboxylate salt by reacting a metal oxide, metal bicarbonate, metal carbonate, or metal hydroxide with a dithiolane carboxylic acid in a lower alcohol solution, as disclosed by Trusovs in U.S. Pat. No. 6,670,494. A preferred dithiolane carboxylate salt is magnesium lipoate, the magnesium salt of lipoic acid, wherein n is 4. Lipoic acid (Chemical Abstracts Service Registry No. 62-46-4; principal names: alpha-lipoic acid, thioctic acid and 1,2-dithiolane-3-pentanoic acid) is the starting material for the preparation of magnesium lipoate as disclosed above. Lipoic acid is a chiral compound that was first isolated and identified in 1950. The compound is commercially available as racemic α-lipoic acid, enantiopure R-(+)- or S-(−)-α-lipoic acid, mixtures thereof, as well as the reduced counterpart racemic dihydrolipoic acid (6,8-dimercaptooctanoic acid), enantiopure R-(−)- or S-(+)-dihydrolipoic acid, and mixtures thereof. In accordance with the present invention, the term "magnesium lipoate" includes the magnesium salt of racemic α-lipoic acid, enantiopure R-(+)- or S-(−)-α-lipoic acid, mixtures thereof, as well as the reduced counterpart racemic dihydrolipoic acid (6,8-dimercaptooctanoic acid), enantiopure R-(−)- or S-(+)-dihydrolipoic acid, and mixtures thereof.

According to the method of the present invention, the composition of the present invention is administered, alone or in combination with other substances (e.g., along with materials necessary to form a tablet or caplet as a delivery vehicle for the composition or in a hard gelatin capsule) in sufficient quantities to reduce phosphorus absorption from the gastrointestinal tract. The composition is administered orally, preferably close in time to food and/or beverage consumption (i.e., concurrent with and/or within about 1 hour before or after ingestion of food or beverages). The composition is ingested after sprinkling or distributing on or in food or beverages, either before or after food preparation, or is ingested as a pharmaceutical dosage form, preferably a tablet, caplet or capsule.

The term "excipient material" is intended to mean any compound forming a part of the formulation which is not intended to have biological activity itself and which is added to a formulation to provide specific characteristics to the dosage form, including by way of example, providing protection to the active ingredient from chemical degradation, facilitating release of a tablet or caplet from equipment in which it is formed, and so forth.

By the terms "treating" and "treatment" and the like are used herein to generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein encompasses any treatment of a disease in a mammal, particularly a human and includes: (a) preventing the disease from occurring in a subject which may be predisposed to the disease but has not yet been diagnosed as having it; (b) inhibiting the disease or arresting its development; (c) relieving the disease, causing regression of the disease and/or its symptoms or conditions; or (d) returning a clinical value to the concentration range normally found in a subject.

The phrase "therapeutically effective" is intended to qualify the amount of the composition of the present invention for use in the orally administered therapy which will achieve the goal of reducing elevated serum phosphorus levels by controlling, abating, ameliorating, reducing or preventing, for example, the absorption of phosphorus from ingesta in the gastrointestinal tract, while avoiding adverse side effects typically associated with metal-containing phosphorus binding agents.

Included within the scope of this invention is a method of treating hyperphosphatemia in a warm-blooded animal using pharmaceutical compositions comprising a combination of cationic phosphate binders, and a suitable pharmaceutical carrier.

For the purpose of this disclosure, a warm-blooded animal is a member of the animal kingdom which includes but is not limited to mammals and birds. The most preferred mammal of this invention is human.

Phosphorus binding is a chemical reaction between a cationic phosphate binder and dietary phosphorus, which encompasses both inorganic and organic anions of phosphorus in the various forms that are capable of electrostatic reaction with a cationic phosphate-binding agent including, by way of example, phosphate ($H_2PO_4^{1-}$, $HPO_4^{2-}$, and $PO_4^{3-}$), pyrophosphate ($P_2O_7^{4-}$), resulting in the formation of insoluble and hence unabsorbable phosphate compounds; adsorption of phosphorus-containing anions on the surface of binder particles; or a combination of both processes. In general, conventional phosphate binders comprise a single cationic substance, i.e., a calcium salt, a magnesium salt, a lanthanum salt, an aluminum salt, or a cationic polymer effective for phosphate binding such as RenaGel® (Genzyme Corp.). Surprisingly, the inventor has discovered that a composition comprising a first L-carnitine alkaline earth metal salt of an organic acid together with a second phosphate binder comprising a member of the group consisting of a conventional Pi binder, a second L-carnitine alkaline earth metal salt of an organic acid different from the first, and a dithiolane carboxylate having the formula:

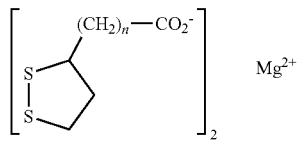

wherein n is an integer from 1 to 8, provides unexpected and synergistic phosphorus binding action as well as significant and distinct pluripotent therapeutic benefits to a subject requiring treatment for hyperphosphatemia, as compared to conventional Pi binders.

One embodiment of the present invention, for example, is a composition comprising L-carnitine, a calcium salt and a magnesium dithiolane carboxylate salt. In this embodiment, the L-carnitine, the calcium ion and the magnesium ion bind phosphorus in ingesta and prevent its absorption from the gastrointestinal tract. Preferred embodiments of the present invention include compositions in which the calcium salt is calcium acetate, calcium carbonate, calcium citrate, calcium alginate, calcium gluconate, calcium lactate, calcium sulfate, calcium succinate, or combinations thereof, and the magnesium salt is magnesium lipoate. More preferred embodiments of the present invention comprise a first quantity of a hydrophilic calcium salt (Table 1) selected from the group consisting of calcium acetate, calcium gluconate, calcium lactate, calcium succinate, or combinations thereof, and a second quantity of the dithiolane carboxylate salt, a lipophile that binds phosphate and has therapeutically beneficial antioxidant properties. Such a more preferred composition provides a cationic phosphate binder that is a hydrophile (in other words, a cationic phosphate binder that has a solubility in water that exceeds about 0.5 g/100 mL of water) and binds phosphate in hydrophilic environments and a second, lipophilic phosphate binder, the metal dithiolane carboxylate, which binds phosphate in lipophilic environments.

TABLE 1

Examples of Cationic Phosphate Binders that are Relative Hydrophiles*

| Metal Salt | Solubility in Water | Hydrophile? |
|---|---|---|
| Calcium Acetate | 37.4 g/100 mL | Yes |
| Calcium Carbonate | 0.0013 g/100 mL | No |
| Calcium Citrate | 0.10 g/100 mL | No |
| Calcium Gluconate | 3.72 g/100 mL | Yes |
| Calcium Lactate | 5.4 g/100 mL | Yes |
| Calcium Succinate | 1.28 g/100 mL | Yes |
| Calcium Sulfate | 0.20 g/100 mL | No |
| Lanthanum Sulfate | 2.92 g/100 mL | Yes |
| Magnesium Acetate | 53.4 g/100 mL | Yes |
| Magnesium Carbonate | 0.01 g/100 mL | No |
| Magnesium Hydroxide | 0.00125 g/100 mL | No |
| Magnesium Lactate | 4 g/100 mL | Yes |
| Magnesium Oxide | No measurable solubility | No |
| Magnesium Sulfate | 27.2 g/100 mL | Yes |

*Data are taken from Lange's Handbook of Chemistry, 15th edition, Dean J A, ed. McGraw Hill, Inc., New York, 1999.

Preferred embodiments of the present invention include compositions comprising an L-carnitine calcium salt and an L-carnitine magnesium salt. The advantages of such embodiment of the present invention as compared to conventional phosphate binders include the following: (a) Each of the cationic components of the composition, namely L-carnitine, calcium ion and magnesium ion, binds phosphorus in ingesta and prevents its absorption from the gastrointestinal tract. (b) The composition provides L-carnitine in an odorless and tasteless form that does not interfere with its fractional absorption from the gastrointestinal tract or its retention in the gastrointestinal tract. (c) The quantity of calcium salt in this embodiment is independent of the quantity of the magnesium salt of the present invention. Advantageously, therefore, the quantity of calcium salt that is employed may be selected to maximize phosphorus binding and minimize transfer of calcium ion to the systemic circulation, uptake that is believed to cause vascular calcification. Further, the quantity of magnesium salt that is employed may be selected to maximize phosphorus binding and minimize transfer of magnesium ion to the systemic circulation, uptake that is believed to cause hypermagnesia. (d) The quantity of calcium salt and the quantity of magnesium salt in this embodiment may be selected to maximize phosphorus binding and minimize the side effects of constipation caused by calcium ion and the side effects of diarrhea caused by magnesium ion. (e) The quantity of calcium salt and the quantity of magnesium salt in this embodiment may be selected to maximize phosphorus binding and minimize the side effects of kidney dysfunction and bone disorders.

Most preferred embodiments of the present invention include compositions comprising an L-carnitine calcium salt and magnesium (R)-(+)-lipoate. The advantages of such embodiment of the present invention as compared to conventional phosphate binders include the following: (a) Each of the cationic components of the composition, namely L-carnitine, calcium ion and magnesium ion, binds phosphorus in ingesta and prevents its absorption from the gastrointestinal tract. (b) The composition provides L-carnitine in an odorless and tasteless form that does not interfere with its fractional absorption from the gastrointestinal tract or its retention in the gastrointestinal tract. (c) The quantity of calcium salt in this embodiment is independent of the quantity of the magnesium salt of the present invention. Advantageously, therefore, the quantity of calcium salt that is employed may be selected to maximize phosphorus binding and minimize transfer of calcium ion to the systemic circulation, uptake that is believed to cause vascular calcification. Further, the quantity of magnesium salt that is employed may be selected to maximize phosphorus binding and minimize transfer of magnesium ion to the systemic circulation, uptake that is believed to cause hypermagnesia. (d) The quantity of calcium salt and the quantity of magnesium salt in this embodiment may be selected to maximize phosphorus binding and minimize the side effects of constipation caused by calcium ion and the side effects of diarrhea caused by magnesium ion. (e) The quantity of calcium salt and the quantity of magnesium salt in this embodiment may be selected to maximize phosphorus binding and minimize the side effects of kidney dysfunction and bone disorders. (f) The composition provides lipoate, an entity which is known to have beneficial health and therapeutic activities.

A preferred composition of the present invention comprises a first quantity of an L-carnitine calcium salt and a second quantity of an L-carnitine magnesium salt, wherein the combination of the first quantity and the second quantity comprises a therapeutically effective quantity of a phosphate-binding composition of the present invention. Another preferred composition of the present invention is a composition comprising a first quantity of an L-carnitine calcium salt and a second quantity of magnesium lipoate, wherein the combination of the first quantity and the second quantity comprises a therapeutically effective quantity of a phosphate-binding composition of the present invention. A particularly preferred composition of the present invention is a composition comprising a first quantity of an odorless and tasteless L-carnitine calcium salt and a second quantity of magnesium (R)-(+)-lipoate, wherein the combination of the first quantity and the second quantity comprises a therapeutically effective quantity of a phosphate-binding composition of the present invention.

A preferred composition of the present invention comprises a first quantity of an L-carnitine calcium salt and a second quantity of a dithiolane carboxylate salt, wherein the combination of the first quantity and the second quantity comprises a therapeutically effective quantity of a phosphate-binding composition of the present invention. A more preferred composition of the present invention is a composition comprising a first quantity of an L-carnitine calcium salt and a second quantity of magnesium lipoate, wherein the combination of the first quantity and the second quantity comprises a therapeutically effective quantity of a phosphate-binding composition of the present invention. A particularly preferred composition of the present invention is a composition comprising a first quantity of an odorless and tasteless L-carnitine calcium salt and a second quantity of magnesium (R)-(+)-lipoate, wherein the combination of the first quantity and the second quantity comprises a therapeutically effective quantity of a phosphate-binding composition of the present invention.

While not intending to be bound by any hypothesis or theory, the inventor believes that the Pi binder compositions of the present invention provide significant advantages over conventional Pi binders. For several decades it has been known that exogenous L-carnitine may be ingested as a dietary or nutritional supplement. Conventional L-carnitine supplements, however, suffer from the disadvantages that L-carnitine has an objectionable odor and taste, is a hygroscopic substance that exhibits poor storage stability, and has a bioavailability from the gastrointestinal tract of 3% to about 18% (i.e., as little as 3% to about 18% of the administered dose is transferred from the gastrointestinal tract to the systemic circulation). No physiological benefit to the unabsorbed 82% to 97% of the ingested L-carnitine has been described in the published literature, nor has a beneficial time of administration been disclosed in published reports. After lengthy investigations, the inventor has discovered that ingested L-carnitine provides dual benefits to the individual receiving it orally: a small portion of it is absorbed from the gastrointestinal tract and increases the systemic concentrations of L-carnitine, and a majority of the oral dose is retained in the gastrointestinal tract, where it binds dietary Pi. Further, the inventor has discovered odorless and tasteless forms of L-carnitine which provide L-carnitine and either of two other Pi binders, $Ca^{2+}$ and $Mg^{2+}$. These odorless and tasteless L-carnitine compositions comprise L-carnitine calcium salts and L-carnitine magnesium salts which after ingestion, provide L-carnitine, $Ca^{2+}$ and $Mg^{2+}$ having activities as Pi binders in the gastrointestinal tract and beneficial physiological and therapeutic activities after absorption from the gastrointestinal tract. Likewise, the inventor has discovered that combinations of odorless and tasteless L-carnitine calcium salts and Mg dithiolane carboxylate salts provide, after ingestion, L-carnitine, Ca, and Mg having activities as Pi binders in the gastrointestinal tract and beneficial physiological and therapeutic activities after absorption from the gastrointestinal tract. Finally, the inventor has discovered that the beneficial actions of these combinations of Pi binders are optimized if the combination is ingested close in time to eating or drinking (i.e., within about an hour of eating or drinking).

Dosage Forms. The compositions of this invention can be administered by any means that effects contact of the therapeutically active ingredients (i.e., active ingredients) with the site of action in the body of a warm-blooded animal. A most preferred administration is by the oral route (i.e., ingestion). The active ingredients can be administered by the oral route as particles that are sprinkled or distributed on or in food or are dissolved or suspended in beverages or can be provided in pharmaceutical solid dosage forms, such as tablets, capsules, and powders, or in liquid dosage forms, such as elixirs, syrups, and suspensions. The pharmaceutical composition is preferably made in the form of a dosage unit containing a particular amount of each active ingredient.

In general, the pharmaceutical compositions of this invention can be prepared by conventional techniques, as are described in *Remington's Pharmaceutical Sciences*, a standard reference in this field [Gennaro A R, Ed. *Remington: The Science and Practice of Pharmacy.* 20$^{th}$ Edition. Baltimore: Lippincott, Williams & Williams, 2000]. For therapeutic purposes, the active components of this invention are ordinarily combined with one or more excipients appropriate to the indicated route of administration. Such capsules or tablets may contain a controlled-release formulation as may be provided in a dispersion of active compound in hydroxypropyl methylcellulose or related material known to alter the kinetics of release of the active agent. Solid dosage forms can be manufactured as sustained release products to provide for continuous release of medication over a period of hours using known pharmaceutical techniques. Compressed tablets can be sugar coated or film coated to mask any unpleasant taste and protect the tablet from the atmosphere, or enteric coated for selective disintegration in the gastrointestinal tract. Both the solid and liquid oral dosage forms can contain coloring and flavoring to increase patient acceptance.

Serum phosphorus levels rise easily after a large meal. Therefore, dosing for oral administration preferably comprises a regimen calling for administration of a therapeutic dose of calcium succinate close in time to the ingestion of food and/or beverages. Dosing may be subdivided in a manner in which a portion of the prescribed dose is ingested prior to consumption of food or beverages, another portion is ingested together with food or beverages, and yet other portions are ingested close in time after ingestion of food or beverages. Preferably, dosing occurs within about an hour prior to and after ingestion of food or beverages.

Without further elaboration, it is believed that one skilled in the art can, using the preceding description, utilize the present invention to its fullest extent. The following specific embodiments are, therefore, to be construed as merely illustrative, and not limitative of the remainder of the disclosure in any way whatsoever.

EXAMPLE 1

In Vitro Assessment of Phosphate (Pi) Binding by a Pi Binding Composition of the Present Invention Test Preparations: Solutions of the test article (a combination of L-carnitine calcium acetate and L-carnitine magnesium citrate) and control articles (calcium acetate) are prepared in deionized, purified water having 18 MΩ or greater resistance. The pH of each solution is adjusted to the desired value by the addition of concentrated hydrochloric acid or sodium hydroxide, as appropriate.

Tests and Assays: Calcium is assayed as described in the U.S. Pharmacopoeia by dissolving an accurately weighed sample in water containing hydrochloric acid, adding hydroxynapthol blue as an indicator, and titrating to a blue endpoint with edetate disodium solution. An HPLC method with conductivity detection was developed and validated for use in the determination of acetate and phosphate. The separation was performed on a Dionex AS11 Cation-Exchange HPLC column integrated with an Agilent Series 1100 HPLC system, and detection of the anionic species was enabled using a Dionex ED50 Electrochemical Detector, operating in Conductivity Mode. Limits of Detection and Quantitation were enhanced through the use of a Dionex Anion Self-Regenerating Suppressor. After assay-specific development and verification of assay performance were completed, the analysis of phosphate and acetate was performed by sampling the test solution and diluting it, if necessary, to a concentration within the linear range of the Assay. The sample was then injected onto the HPLC column and eluted with a sodium hydroxide gradient. Data were acquired using Agilent ChemStation® software.

Experimental Methods: 1.43 g of $NaH_2PO_4 \cdot H_2O$ (equivalent to 329 mg of elemental phosphorus present as phosphate) was dissolved in 570 mL of deionized water. The test or control binder is dissolved in deionized water to a volume of 30 mL. The binder solution will be added to the phosphorus solution to give a final volume of 600 mL. For each binder study, the phosphorus solutions will be titrated by addition of concentrated HCl or NaOH to two different initial pH levels: 4 and 6. Published reports indicate that a drift in pH over time may be observed, and the solutions will be re-titrated to their initial pH immediately after addition of the binder solution and again 1 and 24 h thereafter. During titrations the mixture will be stirred with a magnetic stirrer at ~100 rpm for ~1 min. Then the beakers containing the solutions will be covered with plastic wrap and placed in a shaker bath at 37° C., shaking at ~20 cycles per minute. This stirring rate was selected because in vitro antacid activity at such low stirring rates has been reported to correlate well with in vivo antacid activity in the stomach. Samples for the HPLC assay of acetate and Pi will be taken just before titrations to the initial pH and at 1, 4, and 10 h post-mixing; these later intervals have been reported to correspond to the approximate residence time in stomach, the time available for absorption in the small intestine, and the maximum time available for phosphorus binding that have been reported in related in vivo studies, respectively. Then the samples will be centrifuged at 3,000 rpm for 30 min. The supernatant will be filtered sequentially though filter paper (#50; Whatman, Inc., Clifton, N.J.) and then through a 0.2 μm pore-size filter (e.g., Millipore Corp., Medford, Mass.) before analysis. (No interference by the filtration processes was observed in preliminary experiments.) The decrease in phosphorus concentration from the original concentration in the phosphorus solution to that of the filtrate represents the bound phosphorus. This will be expressed as percent of the total phosphorus present in the original solution. The experiments will be stopped when either 100% phosphorus binding is achieved, or no more than 5% increase in binding is observed over a 6-7 day period of further incubation.

The experimental data are expected to show that the extent of phosphate binding at each value of solution pH by the composition of the present invention is equal to or greater than that of calcium acetate (Table 3).

TABLE 3

Observed in vitro Pi binding for calcium compounds at pH 6

| Pi Binder | % Ca, by weight | Observed in vitro Pi Binding, % | | Comments |
|---|---|---|---|---|
| | | pH 4.0 | pH 6.0 | |
| Calcium Acetate | 23% | 58.6% | 93.8% | Inventor's findings (Note 1); confirm data of Sheikh et al. (Note 2) |
| Present invention | ND | | | Inventor's discovery (Note 1) |
| Calcium Carbonate | 40% | Not Reptd. | 90 | (Note 2) |
| Calcium Citrate | 21% | Not Reptd. | 10 | 20% at pH 6.5 (Note 2) |
| Calcium Formate | 31% | Not Reptd. | Not Reptd. | Not reported. |
| Calcium Lactate | 14% | Not Reptd. | 90 | (Note 2) |
| Calcium Gluconate | 9.3% | Not Reptd. | 90 | (Note 2) |

(Note 1): Mean values of triplicate determinations of phosphate and acetate by anion-exchange HPLC with conductivity detection.
(Note 2): Sheikh M S, Maguire J A, Emmett M, Santa Ana C A, Nicar M J, Schiller L R, Fordtran J S. Reduction of dietary phosphorus absorption by phosphorus binders: A theoretical, in vitro, and in vivo study. J Clin Invest 1989; 83: 66-73.

The data in Table 3 are expected to confirm that Pi binding by both calcium acetate and a composition of the present invention occurs at values of pH as low as pH 4.0 but is nearly quantitative at values of pH near neutrality. Note as well that these in vitro data fail to predict the differences in Pi binding by the various calcium salts that are observed in vivo, nor do these in vitro data reveal the poor dissolution of calcium carbonate in the stomach and the "vinegar breath" associated with ingestion of calcium acetate. Neither of these shortcomings is observed when a composition of the present invention is used as a Pi binder.

Similar in vitro studies have been completed to show that calcium and aluminum salts are effective phosphate binders. [Sheikh M S, Maguire J A, Emmett M, Santa Ana Calif., Nicar M J, Schiller L R, Fordtran J S. Reduction of dietary phosphorus absorption by phosphorus binders: A theoretical, in vitro, and in vivo study. J Clin Invest 1989; 83:66-73.] A study by Fine et al. confirms that magnesium salts are phosphate binders. [Fine K D, Santa Ana C A, Porter J L, Fordtran J S. Intestinal absorption of magnesium from food and supplements. J Clin Invest 1991; 88: 396-402.] Likewise, similar in vitro studies have been completed to show that cationic polymers are effective phosphate binders. [Bleyer A J, Burke S K, Dillon M, et al. A comparison of the calcium-free phosphate binder sevelamer hydrochloride with calcium acetate in the treatment of hyperphosphatemia in hemodialysis patients. Am J Kidney Dis 1999; 33: 694-701.]

The following example presents hypothetically useful therapeutic applications of representative pharmaceutical compositions of the present invention and their anticipated outcomes in treating hyperphosphatemia in subjects requiring such treatment. The examples are representative of the scope of the invention, and as such are not to be considered or construed as limiting the invention recited in the appended claims.

EXAMPLE 2

In Vivo Phosphorus Binding by Representative Compositions of the Present Invention In vivo phosphorus binding by a composition of the present invention (a test composition) and a placebo will be assessed in 10 healthy human subjects. Each subject will be studied on three separate test days: fast, placebo, and a test composition. Five representative embodiments of compositions of the present invention (in other words, five test compositions) will be evaluated in independent studies: Embodiment 1 in which the test composition comprises a first quantity of L-carnitine calcium acetate and a second quantity of L-carnitine magnesium citrate, wherein the combination of the first quantity and the second quantity equals a quantity of the composition that is therapeutically effective for binding phosphate in ingesta. Embodiment 2 in which the test composition comprises a first quantity of L-carnitine calcium succinate and a second quantity of magnesium lipoate, wherein the combination of the first quantity and the second quantity equals a quantity of the composition that is therapeutically effective for binding phosphate in ingesta. Embodiment 3 in which the test composition comprises a first quantity of L-carnitine calcium acetate and a second quantity of magnesium lipoate, wherein the combination of the first quantity and the second quantity equals a quantity of the composition that is therapeutically effective for binding phosphate in ingesta. Embodiment 4 in which the test composition comprises a first quantity of L-carnitine calcium acetate and a second quantity of sevelamer hydrochloride, wherein the combination of the first quantity and the second quantity equals a quantity of the composition that is therapeutically effective for binding phosphate in ingesta. Embodiment 5 in which the test composition comprises a first quantity of the cationic polymer known as RenaGel® and a second quantity of L-carnitine calcium acetate, wherein the combination of the first quantity and the second quantity equals a quantity of the composition that is therapeutically effective for binding phosphate in ingesta.

On each day, subjects will be prepared by a mannitol-electrolyte gastrointestinal lavage, in order to cleanse the gastrointestinal tract. Four hours after completion of the washout, subjects will consume 25 mEq of the test composition or a placebo (lactose) with 100 mL of deionized water. On one of the test days (the fast day), subjects will ingest no meal, placebo or the test composition; the rest of the procedure will be the same. Then each subject will eat a test meal of 80 g ground sirloin steak, 100 g French fried potatoes, 30 g Swiss cheese and 250 mL water containing 10 g of polyethylene glycol (PEG3500) as a non-absorbable marker. After the meal, each subject will consume 25 mEq of the test composition, in the same form as will have been consumed prior to the meal, or additional placebo, with 100 mL of water. Duplicate meals will be prepared (one for consumption and one to be analyzed for phosphorus). The duplicate meals will be analyzed for phosphorus and are expected to contain about 350 mg of phosphorus.

Each test composition will be administered in gelatin capsules that contain the test composition. The total dose will equal 50 mEq of the test composition, one half of the dose (25 mEq) taken just before the meal and the other half immediately after the meal. On one test day a placebo will be taken instead of the test composition. The order of testing will be randomized.

Ten hours after a meal, a second lavage will be begun, using the procedure described above. This will remove unabsorbed material from the gut. All urine voided during the 10-hour period will be collected and analyzed for phosphorus. Rectal effluent will be collected, pooled with any stool passed during the 10-hour period and analyzed for phosphorus. Absorption will be calculated according to the following equation:

$$\text{Net phosphorus (P) absorption}=(\text{P content of duplicate meal, mg})-(\text{Total Effluent P, mg})$$

The results are expected to demonstrate that each test composition results in the inhibition of phosphorus absorption, when ingested close in time to food and beverage consumption. In other words, it is anticipated that on the placebo day, as much as about 70% or more of the dietary phosphorus will be absorbed from the GI tract of each subject. By comparison, on the day in which a test composition is ingested close in time to food and beverage consumption, it is anticipated that as little as about 20% of dietary phosphorus will be absorbed.

I claim:

1. A composition for reducing the amount of dietary phosphorus absorbed from the alimentary tract comprising a combination of L-carnitine and at least one other cationic phosphate binder, wherein the cationic phosphate binder is sevelamer.

2. A composition for reducing the amount of dietary phosphorus absorbed from the alimentary tract comprising a combination of L-carnitine and at least one other cationic phosphate binder, wherein the cationic phosphate binder is a cationic polymer.

3. The composition of claim 1, wherein the phosphate-binding activity of said composition is optimized by administration by ingestion with food or by ingestion close in time to the consumption of dietary phosphate-containing food or beverage by a mammal.

4. The composition of claim 2, wherein the phosphate-binding activity of said composition is optimized by administration by ingestion with food or by ingestion close in time to the consumption of dietary phosphate-containing food or beverage by a mammal.

\* \* \* \* \*